United States Patent [19]
Klatzmann et al.

[11] Patent Number: 5,948,675
[45] Date of Patent: Sep. 7, 1999

[54] HOST-VECTOR SYSTEM WHICH CAN BE USED IN GENE THERAPY

[75] Inventors: David Klatzmann; Jean-Loup Salzmann, both of Paris, France

[73] Assignee: Universite Pierre et Marie Curie (Paris VI), Paris, France

[21] Appl. No.: 08/696,941

[22] PCT Filed: Feb. 22, 1995

[86] PCT No.: PCT/FR95/00208

§ 371 Date: Oct. 4, 1996

§ 102(e) Date: Oct. 4, 1996

[87] PCT Pub. No.: WO95/22617

PCT Pub. Date: Aug. 24, 1995

[30] Foreign Application Priority Data

Feb. 22, 1994 [FR] France .................................. 94 01994
Dec. 15, 1994 [FR] France .................................. 94 15135

[51] Int. Cl.$^6$ .................................................. C12N 15/00
[52] U.S. Cl. ..................... 435/320.1; 514/44; 424/93.21; 435/69.1; 435/325; 435/455; 536/23.1
[58] Field of Search .......................... 514/44; 435/173.3, 435/320.1, 69.1, 325, 235, 455; 424/93.21; 935/23, 32, 52, 57; 536/23.1

[56] References Cited

U.S. PATENT DOCUMENTS

| | | | |
|---|---|---|---|
| 4,650,764 | 3/1987 | Temin et al. | 435/325 |
| 4,920,209 | 4/1990 | Davis et al. | 435/235 |
| 5,124,263 | 6/1992 | Temin et al. | 435/325 |
| 5,587,308 | 12/1996 | Carter et al. | 435/325 |
| 5,591,624 | 1/1997 | Barber et al. | 435/325 |
| 5,648,254 | 7/1997 | Mulvihill et al. | 435/217 |
| 5,741,486 | 4/1998 | Pathak et al. | 424/93.21 |

FOREIGN PATENT DOCUMENTS

| | | |
|---|---|---|
| WO 88/01291 | 2/1988 | WIPO . |
| WO 90/02176 | 3/1990 | WIPO . |
| WO 90/02806 | 3/1990 | WIPO . |
| WO 90/12087 | 10/1990 | WIPO . |
| WO 91/19803 | 12/1991 | WIPO . |
| WO 92/05266 | 4/1992 | WIPO . |
| WO 93/04167 | 3/1993 | WIPO . |

OTHER PUBLICATIONS

Bosselman, R.A., et al, *Molecular and Cellular Biology*, vol. 7, No. 5, pp. 1797–1806, May 1987 "Replication–Defective Chimeric Helper Proviruses and Factors Affecting Generation of Competent Virus: Expression of moloney Murine Leukemia Virus Structural Genes via the Metallothionein Promoter".

Markowitz, D., et al, *Virology*, 167, 400–406 (1988) "Construction and use of a Safe and Efficient Amphotropic Packaging Cell Line".

Caruso, M., et al, *Proc. Natl. Acad. Sci.*, vol. 90, pp. 7024–7028, Aug. 1993 "Regression of established macroscopic liver metastases after in situ transduction of a suicide gene".

Takahara, Y., et al, *Journal of Virology*, vol. 66, No. 6, pp. 3725–3732, Jun. 1992 "A New Retrovirus Packaging Cell for Gene Transfer Constructed from Amplified Long Terminal Repeat–Free Chimeric proviral Genes".

Rich, D.P., et al, *Human Gene Therapy*, 4:461–476 (1993) "Development and Analysis of Recombinant Adenoviruses for Gene Therapy of Cystic Fibrosis".

Nahreini, P., et al, *Gene*, 119 (1992) 265–272 "Cloning and integration of DNA fragments in human cells via the inverted terminal repeats of the adeno–associated virus 2 genome".

Joyner, A.L., et al, *Molecular and Cellular Biology*, vol. 3, No. 12, pp. 2180–2190, Dec. 1983 "Retrovirus Transduction: Generation of Infectious Retroviruses Expressing Dominant and Selectable Genes Is Associated with In Vivo Recombination and Deletion Events".

Markowitz et al. (J. Vir., vol. 62, 4:1120–1124, 1992).

Curiel et al. (Human Gene Therapy 3:147–154, 1992).

Rich et al., Hum. Gene, Ther., 1993, 4:461–476, 1993.

Gheysen et al., Cell, 1989, 59, 1:103–112, 1989.

Caruso et al., P.N.A.S., 1993, vol. 71:7024–7028, 1993.

Shelz et al., Current Topics in Microbiology and Immunology, 1984, vol. 111:1–39.

Armentano et al., Hum. Gene. Ther., 1995, 6:1343–1353, 1995.

Miller et al., The FASEB J., 1995, vol. 9:190–199, 1995.

Harris et al., TIG, 1996, vol. 12, 10:400–405, 1996.

Ronal Crystal, Science, 1995, 270: 404–409, 1995.

Coghlan, New Scientist, 1995, 148: 14–15, 1995.

Mastrangelo et al., Seminars in Oncology, 1996, vol. 23, No. 1:4–21, 1996.

Noguiez–Hellin et al., P.N.A.S., 1996, vol. 93:4175–4180, 1996.

*Primary Examiner*—Bruce R. Campell
*Assistant Examiner*—Dave Trong Nguyen
*Attorney, Agent, or Firm*—Nixon & Vanderhye PC

[57] ABSTRACT

The invention relates to a system for expressing a transgene in a target cell or a human or animal cell, characterized in that it consists of a eukaryotic cell established as a line, into which there have been transfected:

a) a recombinant viral sequence in which a gene has been deleted totally or partially and substituted by the transgene at the level of this gene;

b) a nucleic acid sequence including a sequence encoding the deleted protein, which sequence is in dependence on a promoter and is combined, where appropriate, with the transgene, and flanked at its 3' end a polyadenylation site;

the recombinant viral genome and the sequence, carried by one or two plasmid supports, being capable of trans-complementing each other and allowing the host cell to produce defective infectious viruses.

6 Claims, 5 Drawing Sheets

DEFECTIVE RECOMBINANT MOLONEY VIRUS

TRANS-COMPLEMENTING SEQUENCE

"WILD-TYPE" MOLONEY VIRUS

HOST-VECTOR SYSTEM WHICH CAN BE USED IN GENE THERAPY

This application represents the U.S. national phase of PCT/FR95/00208 which claims priority to French application 94/01994, filed Feb. 22, 1994, and French application 94/15135, filed Dec. 15, 1994.

The present invention relates to a new approach for gene therapy applied especially to the elimination of certain categories of cells, such as tumor cells or certain cells infected by viruses, by the production of recombinant retroviruses from new genetic constructs.

The concept of gene therapy by killer genes or suicide genes has been developed since 1986 by numerous approaches. It involves the expression of a gene, this expression allowing the conversion of a nontoxic substance or a toxic substance by the cell. This concept of gene therapy is applicable and transposable to any gene whose expression in a target cell makes it possible to convert an inactive substance to an active substance, or vice versa, leading either to a destruction (example of the suicide gene), or to a restoration of certain functions.

In all that follows, the application of these concepts to suicide genes is more particularly developed given the accessibility of its experimental use. The transposition of the means of the invention to any type of transgene whose expression leads to the effect of a substance being modified in the direction of an activation or inactivation is nevertheless within the capability of persons skilled in the art.

Herpes Simplex virus type I thymidine kinase (HSV1-TK) is the enzyme which has been the subject of the highest number of investigations relating to suicide genes.

This enzyme, which is atoxic for eukaryotic cells, has the characteristic of being able to convert certain nucleoside analogs such as aciclovir (ACV) or ganciclovir (GCV) to monophosphate-containing molecules, of which cellular kinases are normally incapable (G. B. Elion, J. Antimicrob. Chemother. 12:9–17 (1983)). These nucleoside monophosphates are then converted by cellular enzymes to nucleotide triphosphates which can be used during the synthesis of DNA and block the elongation process thereby causing the death of the cell. The nucleoside triphosphate analog is therefore only toxic for dividing cells.

All the advantages which can be gained from the use of this type of conditional toxins can therefore be understood when applied to gene, especially anticancer, therapy.

Firstly, only a conditional toxicity makes it possible to generate stable cell clones producing the pseudo-viral particles capable of producing such a transgene and transferring the suicide gene into the target cells. Indeed, these cells simply have to be cultured in the absence of ACV or GCV since HSV1 thymidine kinase is not toxic for the cell in the absence of these drugs.

Next, in the event of a side effect of the treatment, stopping the administration of ACV or GCV causes the toxicity due to the transgene to cease immediately; in addition, adjustment of the doses of the nucleoside analog makes it possible to selectively destroy the cells strongly expressing the transgene while preserving the cells in which the gene is weakly expressed; this toxicity which is restricted to dividing cells is a great advantage especially for the treatment of cancer cells.

Finally, experimental data in vitro and in vivo have shown that cells not expressing HSV1-TK, but which are in contact with the latter, were also destroyed by the treatment with ACV ("Metabolic Cooperation" or "bystander effect") (Moolten F. L., 1986, Cancer Research, 46:5276–5281 and Culver K. W. et al., 1992, Science 256:1550–1552).

The mechanism of this effect is still not understood, but it is possible that the nucleoside triphosphate analogs can pass from one cell to another via "gap junctions".

Retroviruses appear to be the best vectors for transferring exogenous genes into eukaryotic cells, especially human cells.

However, an essential precondition for the use of retroviruses for therapeutic purposes and especially in gene therapy is to verify the safety of their use.

The principle danger of the use of retroviruses in gene therapy is the possibility of dissemination of a wild-type retrovirus reconstituted in the cell population or tissue considered.

Such a proliferation could lead to multiple integrations of the retrovirus genome into the genome of the infected cells which can lead to all types of genetic disorders.

This type of approach therefore poses the problem of reaching the greatest number of target cells possible, and therefore the capacity of this system to reach the greatest number of tumor cells possible, while ensuring the control of virus proliferation.

Numerous approaches have been established up until now in order to develop packaging cell lines which produce only defective retroviruses carrying the transgene of interest; the development of such cell lines has considerably increased the use of retroviruses in gene therapy by virtue of the safety conferred by these systems.

The first vectors used were retroviral vectors carried by pseudo-retroviral particles having an amphotropic envelope in order to allow their use in different species, and defective in order to control their dissemination. The initial natural virus is generally the Moloney murine virus from which the cis-acting elements and the trans-acting elements have been separated in order to form two defective genomes.

The actual viral vector preserved the essential cis sequences: the LTRs for the control of transcription and integration, the psi sequence necessary for encapsidation, the PB sequence necessary for the viral replication. The viral genes (gag, pol, env) are deleted and replaced by the transgene to be expressed in a target cell placed in principle under its own promoter or under a promoter judged to be more powerful or regulatable.

The retroviral genes gag, pol and env are often integrated into another vector, sometimes called Helper, which is defective for the LTR and POLICE DA_MATH8AwFINP sequences. Their expression allows the encapsidation of the transgene, excluding the genes necessary for the multiplication of the viral genome and for the formation of complete viral particles.

The proviral form of the Helper is in general integrated into the genome of a murine cell line (for example fibroblast NIH/3T3) which acts both as host for the vector and Helper for the functions which it lacks. After transfection of the vector, the cellular strain becomes capable of producing defective infectious viral particles. However, these particles contain only the gene to be transferred (transgene) alone but do not contain the information necessary for the reconstitution of complete viral particles in the target cells. This system is therefore designed to prevent any subsequent propagation of viruses after the first infection, that is to say if the infectious virus carrying the transgene penetrates into a cell lacking the information of the Helper type (gag, pol and env), its production is stopped.

Therefore, conventionally, the packaging cell line is a cell line capable of providing the Helper information in trans relative to the viral genome present in the particle, such that defective infectious viral particles can be reconstituted.

Different packaging systems allowing the production of defective recombinant viruses have been described in the following documents:

Patent Application EP 0,243,204 describes the use of retroviruses as means for packaging any substance in order to cross the membrane of eukaryotic target cells;

Patent Application WO 89/07150 describes a retrovirus packaging cell, both plasmids expressing in trans the different viral genes (env, gag, pol), but none of the two comprising the packaging POLICE DA_MATH8AwFINP sequence; the production of virus in these lines is between 104 and 106 CFU/ml;

Patent Applications WO 90/02806, WO 90/12087, EP 0,476,953, WO 93/04167 and WO 93/10218 are publications describing gene transfers in vivo using retroviral vectors which are themselves produced by packaging cell lines.

The numerous references of constructs and applications cited in these patents are included by way of references cited in the present application.

Recent developments have led to the use of a gene transfer in vivo by directly transferring the vector-producing packaging cell lines for the treatment of tumors; the elimination for example of microscopic experimental cerebral tumors by stereotactic injection of cells producing retroviruses TK-HSV1, followed by treatment with GCV, has been reported by Culver et al. (Science 256:1550–1552, 1992).

Likewise, some of the authors of the present application have shown that, in rats, the in vivo transfer of the HSV1-TK gene by direct injection of murine fibroblasts producing recombinant retroviral particles, leads to a considerable reduction in hepatic tumors in rats (Caruso M. et al., Proc. Natl. Acad. Sci. USA, 90:7024–7028, 1993 and Yves Panis et al., C. R. Acad. SC. Paris,, Tome 315, Series III, p. 541–544); these articles demonstrate, in addition, a very large decrease in the number of cancer cells in the tumors, knowing that, surprisingly, the number of cells transduced in vivo by this type of technique is no doubt less than 10% for TK-HSV1.

This effect could be explained by the metabolic cooperation mechanism already mentioned above.

This system of packaging cell lines allowing the production of viral particles carrying a transgene is therefore extremely promising for use in gene therapy and especially for the expression of conditional genes.

These systems, developed and described in the numerous references cited above, have nevertheless certain limits which are:

1) the low productivity of these cell lines (infectious titer less than or equal to 106 PFU/ml), the normal retrovirus Mo MuLV producing about 108 PFU/ml and a virus such as adenovirus about 109;

2) a second limit of this type of technique is that it uses fibroblast cell lines NIH/3T3 which are adhering lines; this is an advantage when the cell supernatant containing the viral particles is used, but on the other hand is a disadvantage when it is desired to use the transfected lines themselves as medicinal products, the lines injected in vivo producing, in this case, the recombinant viral particles in situ;

3) a third disadvantage, which is the other side of the safety advantage of the system, is that if the viral particles expressed in situ by the packaging cell line can transfer the transgene of interest into the dividing cells, any subsequent dissemination is blocked at this level. This limits the efficiency of the transfer of the transgene because of the blocking of the dissemination.

It was therefore important to design a system which possibly allows self-maintenance of the production of recombinant viral particles carrying the gene of interest while being assured of controlling any subsequent propagation at the chosen time in order to preserve the required safety conditions, namely the total control of the dissemination of the virus in its wild-type form.

In all that follows, the term "transgene" designates the gene to be expressed in the target cell, which gene, in the examples, is of the suicide gene type.

The transgene may also be a cytokine or a molecule of therapeutic interest.

The expression "recombinant pseudo-retroviral sequence" means that the sequence contains all the genes necessary for the expression of a pseudo-retroviral particle with the exception of the envelope (env) gene and possibly comprising one or more transgenes.

The expression "host cell" means the cell containing the two recombinant nucleic acid sequences, which are carried or not by the same plasmid and which is capable of being used either as a medicinal product, or to produce the defective recombinant viruses.

The expression "target cell" means the cell which it is desired to treat by introduction of the transgene.

The present invention addresses and makes it possible to overcome the limits of the abovementioned existing systems by the construction of a host-vector system which makes it possible to express a transgene in a target cell or a human or animal tissue, characterized in that it consists of a eukaryotic cell established as a line, into which there have been transfected:

a) a recombinant pseudo-retroviral sequence in which the env gene has been deleted totally or partially and substituted by the said transgene at the level of the env gene as represented in FIG. 1a, such that the transgene is expressed in spliced transcripts similar to those of the env gene in the wild-type Moloney virus;

b) a nucleic acid sequence including a sequence encoding an envelope or membrane protein, which sequence is in dependence on a promoter and is combined, where appropriate, with the said transgene, and flanked at its 3' end a polyadenylation site and represented in FIG. 1b; the said recombinant viral genome and the said sequence being capable of trans-complementing each other and allowing the said host cell to produce defective infectious viruses lacking the env gene.

The recombinant viral genome described in a) and the nucleic acid sequence carrying the env gene described in b) may be carried either by two different plasmids or transfection systems, either by the same plasmid or transfection system provided that the b) sequence is situated outside the pseudo-retroviral sequence between the two LTRs. A construct on a single plasmid is represented in FIG. 4a.

The characteristic common to both types of approaches: two separate supports or a single support for the a) and b) sequences is that the b) sequence, being devoid of the ψ sequence, is never packaged and consequently the viruses produced by the host are devoid of it.

In addition, in the latter case, the plasmid carrying the two a) and b) sequences or that carrying the pseudo-retroviral sequence of the above FIG. 1a may carry other recombinant sequences intended to enhance the stability or the duration of expression of the said sequences. These complementary elements may be for example the ITRs (for: Inverted Terminal Repeats) of the AAV virus (Adeno Associated Virus). An example of such a construct is represented in FIG. 4b.

It appears clearly in this system that the host cell harbouring the above two recombinant sequences carried by one or two plasmids cannot be likened to a packaging cell line since the first recombinant pseudo-retroviral sequence carries the psi sequence and allows, when it is transfected alone, independently of the second sequence containing the env gene, the production by the host cell of viral particles carrying all the initial sequence, but which are devoid of envelope and therefore noninfectious.

The cell therefore indeed behaves like the host for a normal or recombinant viral vector allowing the production of viral particles without addition of Helper or trans co-expression as described above.

The addition to this host cell of a gene encoding the viral envelope protein in dependence on a promoter and followed by a polyadenylation sequence allows the transcription and then the translation of this gene into protein in the host cell and, subsequently, the reconstitution of viral particles carrying the same genome as the previous ones (and represented in FIG. 1a) with the exception that they now possess an envelope which allows them to infect target cells. These infectious viral particles are, after infection of a target cell, capable of producing infectious viral particles only if the env gene is again added and is expressed.

The recombinant plasmids of the invention which have the characteristics of possessing the recombinant retroviral sequence delimited by the two LTRs, and an env. gene carried or not by the same plasmid support, may also be combined with a system allowing their introduction into the target cells. These systems may be of several types such as viruses or an appropriate vehicle promoting the transfer of the genetic material into the cells; the appropriate vehicles are defined as allowing the crossing of the biological membranes and may be especially liposomes, cationic lipids, polylysine derivatives, inactivated adenoviruses or ballistic methods.

Liposomes have been used to enclose and transfer into cells both nucleic acids and viral particles (R. Philips et al., (1994) Molecular and Cellular Biol. Vol 14 No. 4, p 2411–2418). These vehicles have a very poor efficiency for transfection of the plasmids which they contain. The addition to the pseudo-retroviral sequence of the invention of sequences allowing an enhanced and prolonged expression of the therapeutic sequences of interest makes it possible to envisage their use as recombinant plasmid transporters/carriers or as an intermediate means for the manufacture of a medicinal product, or as active ingredient of a medicinal product; the cell thus transfected by the vehicle containing the vectors then transforms itself into a cell producing defective retroviruses encoding the gene of interest but lacking the envelope gene and the defective virus is itself capable of reinfecting other cells so as to again express therein the gene of interest, the cycle necessarily stopping at this stage, unless an env. sequence is added by any possible means. This cell is either the cell of the host vector system or the target cell as defined above.

The invention also relates to the vehicles as defined above containing a pseudo-retroviral sequence as described in 1a, a recombinant sequence carrying an env. gene as described in 1b, separated or assembled on the same plasmid support as described in FIGS. 4a and 4b, and optionally carrying ITRs of the AAV virus upstream and downstream of the recombinant pseudo-retroviral sequence, and preferably downstream of the recombinant sequence carrying the env. gene.

More generally, any viral vector in which:
a gene essential for the constitution of infectious viral particles is substituted by a transgene of interest,
this essential gene is present on the same vector, or a separate vector, but is not in dependence on viral promoters and,
the product of this gene acts in trans and makes it possible to reconstitute defective viral particles, forms part of the invention.

Another example of a nonretroviral construct of this type is the reconstitution of a defective recombinant adenovirus in which the E1A gene is substituted by a transgene of interest, and the E1A sequence is expressed in trans so as to reconstitute a defective infectious viral particle.

The essential characteristic of the constructs of the invention is that they make it possible to produce infectious viruses either in a host cell, or in a target cell, but the viruses produced will contain a nucleic acid capable of expressing a transgene and incapable of producing infectious particles.

In the case of the pseudo-viral particles described above, the env. sequence will be outside the region for regulating the expression of the retroviral sequences.

This system is particularly advantageous as will be seen later when the transgene to be expressed is a suicide gene, especially the Herpes Simplex virus thymidine kinase (HSV1-TK), or a cytokine.

In the host-vector system of the invention, the recombinant pseudo-retroviral sequence is derived from the genome of the Moloney virus MuLV, the LTR sequences in 5' or 3' being of wild-type origin or derived from different mutants or combinations thereof. There may be mentioned for example the LTR type constructs derived from the mutants mov3, mov9 and mov13 as described in Caruso M. et al. in Proc. Natl. Acad. Sci. USA, 90:7024–7028, 1993.

This nucleic acid sequence (FIG. 1a) which will be encapsidated into the viral particle produced by the host cell, is extremely close to the "wild-type" retroviral genome which offers the advantage of obtaining higher titers than those obtained in the systems described above in the prior state of the art with the packaging cell lines and the trans-complementations of the viral genes.

By way of example, and as will be seen later, whereas in the systems of the state of the art the maximum titer with the packaging cell lines is of the order of $10^6$, this system allows titers of between $10^6$ and $10^9$, and preferably between $10^7$ and $10^8$ PFU/ml.

A second characteristic of the host-vector system of the invention is that the host cell is transfected simultaneously with a nucleic acid sequence including a sequence encoding an envelope protein, this protein being of viral or even retroviral origin, or a membrane or even cellular protein.

"Simultaneously" means that the two sequences, the pseudo-retroviral sequence and the nucleic acid sequence encoding the envelope gene, are expressed simultaneously in the host cell, it being possible to perform the transfections either simultaneously in one or two constructs, or successively.

The envelope gene chosen may be homologous to the pseudo-retroviral sequence, that is to say derived for example from Mo-MuLV, allowing the reconstitution of the homologous pseudo-viral particles or may be derived from another virus, for example and without being limiting the vesicular stomatitis virus (VSV), HIV, the rabies virus or the gibbon leukemia virus, which gene, when it is transcribed and translated into envelope protein, allows the reconstitution of a pseudo-viral type whose envelope is a VSV (or HIV) envelope and the genome containing the LTRs, psi, PB, gag and pol of MuLV, as well as the transgene.

Finally, the env genome may be of cellular origin and may encode a membrane protein allowing the targeting of the viral particle on a specific ligand, especially for a CD4 type receptor.

In addition, the envelope may be a chimeric protein whose carboxy-terminal end is derived from intramembrane sequences of the Moloney envelope. Experimental data indeed exists which shows that these membrane sequences may be involved in the concentration of these envelope proteins at the surface of the viral particle. With these chimeric molecules, the efficiency of expression of the chimeric env protein at the surface of the virions will be increased.

A second advantage of this host-vector system allowing the expression of these heterologous pseudo-viral types is the possibility, where appropriate, of purifying these pseudo-viral particles by ultracentrifugation without loss of infectious power. This makes it possible to obtain viral suspensions whose titer may be as high as 109 PFU/ml.

The nucleic acid sequence containing the env gene as described in FIG. 1b below, may be transfected by any type of means, either physical means or with the aid of viral or retroviral vectors. Among the physical means known, there may be mentioned microinjection, liposomes or alternatively so-called biolistic or bombardment processes as described in Kriegler, M. Gene Transfer and Expression; A Laboratory Manual; MacMillan Publishers Ltd.; 1990.

The transfection may also take place by integrating this nucleic acid sequence into a viral vector and especially an adenovirus.

The advantage of the latter method is the possibility of putting in place a system which is self-maintained in vivo while retaining full control over the viral proliferation.

Indeed, the host-vector system comprising, as transgene, a suicide gene and injected for example in a tumor, will express a recombinant viral particle which will itself reinfect in situ dividing cells.

These cells will in turn reexpress a viral particle, but the latter will not be infectious since the viral genome will not have been trans-complemented by an envelope gene.

If, at this stage, a recombinant expression vector containing the env gene is injected, it will be possible for a new trans-complementation to occur and the cycle is repeated once again; the safety of the system is, in this manner, preserved since a double transfection is necessary, one by the pseudo-viral particle MuLV capable of infecting only dividing cells and the other by the adenovirus capable of infecting all the cells. Therefore, only the dividing cells will be capable of being co-transfected, of expressing the viral genes in trans and of producing pseudo-viral particles capable of infecting the target cells.

This system therefore makes it possible, in a particularly elegant manner, to transfect into a target cell, for example the TK suicide gene, allowing the expression of the latter and conferring on the cell containing it the sensitivity to the nucleoside analogs; the simultaneous transfection of an envelope gene allows the production, by this same target cell, of infectious particles comprising the same recombinant pseudo-viral genome defective in the envelope gene.

This cycle can therefore be repeated the desired number of times as long as the sequence carrying the env gene is provided exogenously; the system stops after one replicative cycle of the virus in the target cell, production of infectious particles, reinfection and production of noninfectious particles.

The whole of this cycle is described in FIG. 2.

A third advantage of the host-vector system according to the invention is that any type of eukaryotic cells established as lines may be chosen provided that this line is capable of producing this type of amphotropic viral particles.

In addition to the NIH/3T3 lines conventionally used to produce recombinant viral particles of the Moloney virus, the host-vector system of the invention allows the use of lines capable of being cultivated in suspension; by way of example, there may be mentioned mouse myelomas, VERO cells or insect cells.

The obvious advantage of using cells in suspension is the industrial application for the preparation of medicinal products which can be used in gene therapy, large quantities of these cells being necessary for such preparations which are obviously much easier to obtain with cells in suspension than with adhering cells.

The choice of VERO cells as host cells may have the advantage, on the one hand, of coming from primates and therefore of being more phylogenetically suitable for man and, on the other hand, of being more resistant to the action of the natural antibodies and of the complement. These cells have finally been used widely for the production of vaccines, and in particular of viruses which undergo only very few inactivation or purification stages (for example vaccine against rabies). Some cells which can be used as viral particle-producing host cells have the property that the said particles are not inactivated by the complement: these are especially human cell lines or lines derived from vison.

The choice, as host cells, of Lepidoptera cells or more generally of insect cells (with the exception of Diptera) also has many advantages for constructing host-vector systems which can be used as medicinal products in gene therapy:

they are capable of producing viral envelope proteins of viruses which infect eukaryotes, but they themselves are not capable of being infected by these viruses;

insect cells do not produce mammalian viruses; viral safety tests relating to them are therefore reduced; these cells are not capable of being infected by viruses which are potentially pathogenic for man; it is therefore safer to use these cells for a use in human therapy from the point of view of viral safety tests;

insect cells grow in suspension and are therefore capable of being cultured on a large scale; insect cells are capable of intratissue movements; consequently, in the case where they might be injected into a tumor, they can therefore move and deliver their pseudo-viral particles at a distance from the site of injection:

it is possible to use promoters specific to insect cells which are strong promoters: for example, it is possible to use baculo virus promoters which give high expression levels and therefore an increased number of pseudo-viral particles;

given that there are several strong promoters derived from baculo virus, it is therefore possible to perform complex constructions in order to limit the risks of recombination between the different transfected genes.

Because of all these advantages, insect cells, optionally modified genetically so as to be capable of manufacturing amphotropic pseudo-viral particles, are a preferred tool for the construction of the host-vector system of the invention.

Persons skilled in the art will know, on a case-by-case basis, depending on the transgene which they wish to express in a target cell, how to produce the constructs using the appropriate expression vectors and the appropriate host cells allowing the trans-complementation of the envelope gene with the retroviral genome carrying the psi sequence, the gag gene, the pol gene and the transgene(s), and allowing dissemination by the addition of the env gene, which is controlled over time and in space.

Another advantageous improvement of the host-vector system of the invention consists in integrating, into the nucleic acid sequence carrying the env gene, a sequence of the HSV1 thymidine kinase gene or any other conditional suicide gene; this improvement is a second key which makes it possible to increase the efficiency of the treatment, as well as the safety of the system, since, in this manner, the suicide gene is expressed in the target cell in dependence on promoters of different types and, consequently, this makes it possible to increase the sensitivity to nucleoside analogs which is conferred on the cells by the expression of this suicide gene.

Another particularly advantageous improvement for the viral safety problems in a therapeutic use in man is the use of a host-vector system in which:

the host cells are insect cells, not producing mammalian viruses;

the vector carrying the env gene used in dependence on a promoter contains upstream of the env gene a homologous sequence of the defective recombinant retrovirus used in the host-vector system, for example all or part of a gag gene or all or part of a pol gene.

This system is advantageous because, if a homologous recombination with a retrovirus occurs in a system where the host contains endogenous retroviruses, for example in mouse cells, then it will lead to the production of nonfunctional retroviruses. This recombination will occur such that the recombinant genome resulting therefrom will also be defective. The injection of this type of cells into man will be completely safe from the viral point of view.

Likewise, the use, with this system, of an insect cell in the host-vector system cannot lead to homologous recombinations, the insect cells not carrying mammalian retroviruses and, consequently, injection for therapeutic purposes will make it possible to produce only the defective recombinant viral particles of the invention, excluding viral particles derived from a homologous recombination and which could then be infectious.

The present invention also relates to a process for expressing a transgene for gene therapy which consists in using the following steps:

a) construction of a host-vector system by transfection, into a eukaryotic host cell, on the one hand, of a pseudo-retroviral sequence in which the env gene is deleted totally and replaced with the transgene, for example at the level of the ATG of the said env gene and, on the other hand, a nucleic acid sequence containing, in its structure, a sequence encoding an envelope protein under the control of a promoter, where appropriate combined with the transgene and flanked at its 3' end by a polyadenylation sequence, the two sequences above being carried by one or two plasmid type vectors, b) bringing the said system into contact with the cells in which the transgene has to be expressed, c) where appropriate, again transferring, into the target cells, the abovementioned sequence containing the env gene. In the case where the two sequences are carried by the same construct, the sequence containing the sequence encoding an env. protein is outside the two 5' and 3' LTRs of the pseudo-retroviral sequence.

In the process of the invention, the transgene may be a gene of therapeutic interest and especially a suicide gene such as the HSV1 thymidine kinase gene which confers, as stated above, the sensitivity of the cells expressing this gene to nucleoside analogs.

In the process of the invention, the pseudoretroviral sequence is directly derived from the Moloney virus MuLV, the LTR sequences in 5' or in 3' being derived directly from specific viral species such as mov9, mov3 or mov13, they may be of wild-type, mutant or combined origin.

In the process of the invention, the sequence containing the env gene is chosen especially from the retrovirus sequences encoding the said gene and especially the env gene of MuLV or the env gene of a heterologous virus such as for example VSV, HIV, the rabies virus, the Gibbon leukemia virus. It goes without saying that the reconstituted viral particle is a hybrid particle whose envelope consists of the envelope protein of the virus from which the env sequence was derived and the viral genome being derived from MuLV.

The process according to the invention is characterized in that the sequence containing the env gene (whether this sequence is included in a plasmid also carrying the pseudo-retroviral sequence or on the contrary whether it is included in an autonomous vector for the latter) is introduced into the target cell by any appropriate means, especially by a viral vector, such as an adenovirus, or alternatively by physical methods, for example bombardment, fusion of liposomes or micro-injection. It goes without saying, as explained above, that the use of an adenovirus allows the implementation of a process with a high yield while preserving total safety since the expression of viral particles can only be achieved in dividing cells and by trans-complementation of the pseudo-viral particle derived from the Moloney virus and of the envelope gene derived from the adenoviral vector.

One advantageous variant of the process of the invention, especially when the liposomes are used as transfection means, is the addition of one or more sequences, outside the two LTRs, whose function would be a function of stabilizing the expression of the pseudo-retroviral sequence and especially of the transgene.

An example of these sequences is the ITR (Invented Terminal Repeat) sequences of the AAV virus. These sequences are capable, when they are present on either side of sequences to be expressed, and especially upstream, of conferring a substantial stabilization of the expression of the said sequences (Philips et al., supra and Flotte T. T. et al. Am. J. Resp. Cell. Mol. Biol, 1992 7: 349).

Apart from this type of sequences, any type of sequence capable of increasing expression in terms of the level and/or duration may be chosen by a person skilled in the art and integrated into the vector or plasmid for transfection outside the two type a) and b) nucleoside sequences above.

More generally, the invention relates to a process which allows the expression of a transgene for gene therapy, characterized by the simultaneous transfection, into target cells, of a retroviral genome having the general structure represented in FIG. 1a, which genome has all the sequences necessary for the expression of a viral particle, but lacks the envelope gene conferring on the said viral particle its infectious character and, on the other hand, a nucleic acid sequence containing, in its structure, a cellular or virus envelope gene, the co-expression in trans of the two sequences thus transfected allowing the expression of recombinant viral particles which are infectious but lack the said env gene in their genome.

This co-expression in trans of the two types of nucleic acid sequences can be achieved either in a host cell therefore allowing the production of a host-vector system which can be used as such in gene therapy, or as a simultaneous injection into the target cells to be treated, or finally by encapsulation into a vehicle, for example liposomes.

This expression may be achieved both when the sequences are carried by two different structures, or by the same plasmid structure provided that the one carrying the env. gene is outside the two 5' and 3' LTRs of the pseudo-retroviral sequence.

The iterative character of the system used is clearly apparent to a person skilled in the art by adding, as required, the second nucleic acid sequence carrying the env gene and capable of being expressed under the control of a promoter.

The invention also relates to the use, in gene therapy, of the host-vector system described above and obtained by simultaneous transfection, into a eukaryotic cell, of two nucleic acid sequences whose expression in trans allows the said eukaryotic cell to produce infectious viral particles carrying the tranagene, it being possible for this use to be advantageously applied to the expression of a suicide gene in target cells to be destroyed.

This co-expression is achieved by a double transfection of sequences described in FIGS. 1a and 1b, or by transfection of a single structure carrying the two types of sequences, 1a and 1b, of which an example is represented in FIG. 4a.

If this single structure carries, in addition, a sequence enhancing the expression in terms of level or duration, such as the ITR sequences of the AAV virus, the use is particularly advantageous, especially in the case of the use of liposomes as means of transfection, thus enhancing the efficiency of this technique and allowing the use of the liposomes carrying recombinant plasmids as intermediate in the manufacture of a host-vector system which can be used in gene therapy or also as active ingredient of medicinal products which can be used in gene therapy.

The AAV ITRs produce their maximum effect when they are positioned one upstream of the 5' LTR and the other downstream of the polyadenylation sequence PA, as represented in FIG. 4b.

Finally, the invention relates to medicinal products which can be used in gene therapy and which are characterized in that they contain, as active ingredient, eukaryotic cells which have been subjected to a double transfection with the nucleic acid sequences as described in FIGS. 1a and 1b; the active ingredient of a medicinal product according to the present invention may also consist, on the one hand, of infectious recombinant viral particles carrying a viral genome in which the env gene has been substituted for example at the level of its initiation codon by the transgene to be expressed and, on the other hand, by a nucleic acid sequence containing, in its structure, the envelope gene, in dependence on a promoter and, where appropriate, flanked by a sequence encoding, for example, the thymidine kinase gene.

The invention likewise relates to medicinal products characterized in that they contain, as active ingredient, liposomes containing recombinant DNA sequences, one of which consists of a pseudo-retroviral sequence between the retrovirus 5' and 3' LTRs, comprising the gag and pol genes and a gene of therapeutic interest, but lacking the env. gene, and another sequence outside the first, containing an env. gene and a polyadenylation sequence and in dependence on a promoter and, where appropriate, also flanked by a sequence encoding a gene of interest; in an advantageous embodiment, the medicinal product consisting of these liposomes carrying recombinant sequences is such that the plasmid carrying them comprises, in addition, sequences which make it possible to enhance the expression of the genes of interest and especially those which are between the two LTRs, thus increasing the efficacy of the said medicinal product.

The gene of interest for the medicinal products of the invention is advantageously the gene for thymidine kinase, which, when it is expressed, confers on the cell harboring it sensitivity to the nucleotide analogs such as gancyclovir or acyclovir.

A person skilled in the art will be able to implement all the possible variants of this type of host-vector system, by routine experimentation.

Such variants, or equivalents, form part of the invention as claimed hereinafter.

The figures and the examples below will make it possible to illustrate the invention more precisely.

BRIEF DESCRIPTION OF DRAWINGS

In this figure:

FIG. 1a represents the defective recombinant Moloney virus in which the grey region represents sequences derived from the Moloney virus and the X gene on a dark background represents the transgene;

FIG. 1b represents a Y gene encoding a viral envelope or a membrane protein flanked in 5' by a promoter and possibly a retrovirus sequence, and flanked in 3' by a polyadenylation sequence;

FIG. 1c, for memory, indicates the sequence of the wild-type Moloney virus.

Figure 1A:
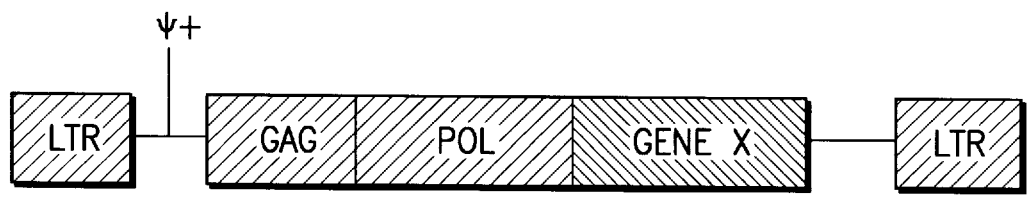
FIGS. 1A–1C represent the construction of the two nucleic acid sequences which are to be transfected simultaneously.

In the first part of the diagram, a vector of the type represented in FIG. 1a is introduced into the host cell. (It should be noted that this introduction may be achieved, either by transfection, or by infection with a defective retroviral particle as described at the end of this diagram). The result of this expression of the vector represented in FIG. 1a is the production of viral particles whose genome is derived from this vector but which do not carry at their surface an envelope protein and which are therefore noninfectious (as represented in the 2nd part of the diagram).

Figure 1B:
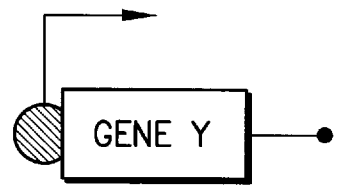
Figure 1C:
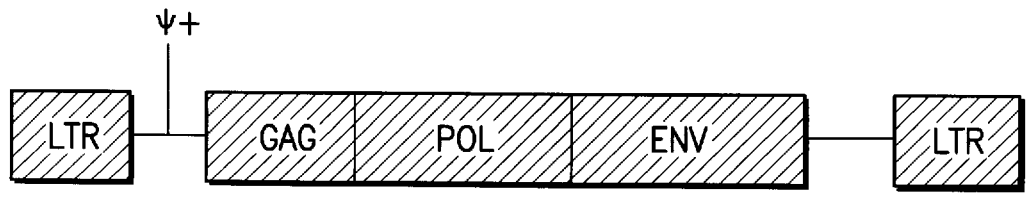

A vector of the type represented in FIG. 1b, carrying the env gene, is then expressed by transfection in this cell. The trans-complementation then allows the expression, at the surface of the viral particles, of the env protein, these viral particles remaining devoid of the env gene.

Figure 2:
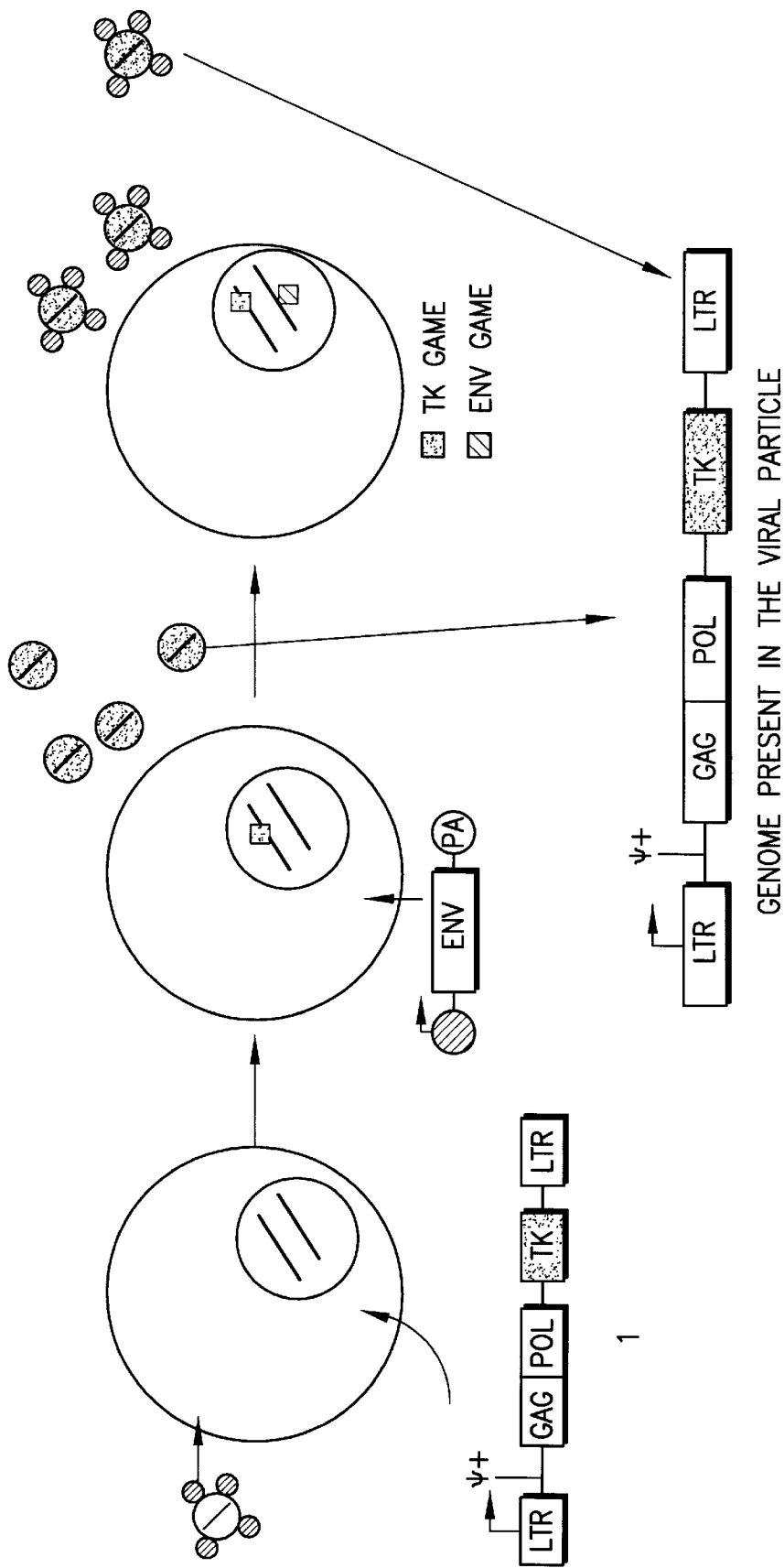
FIG. 2 represents the principle of the co-expression in trans of the production of defective and infectious viral particles allowing the reintroduction, into a target cell, of the defective recombinant retroviral genome.
Figure 3:
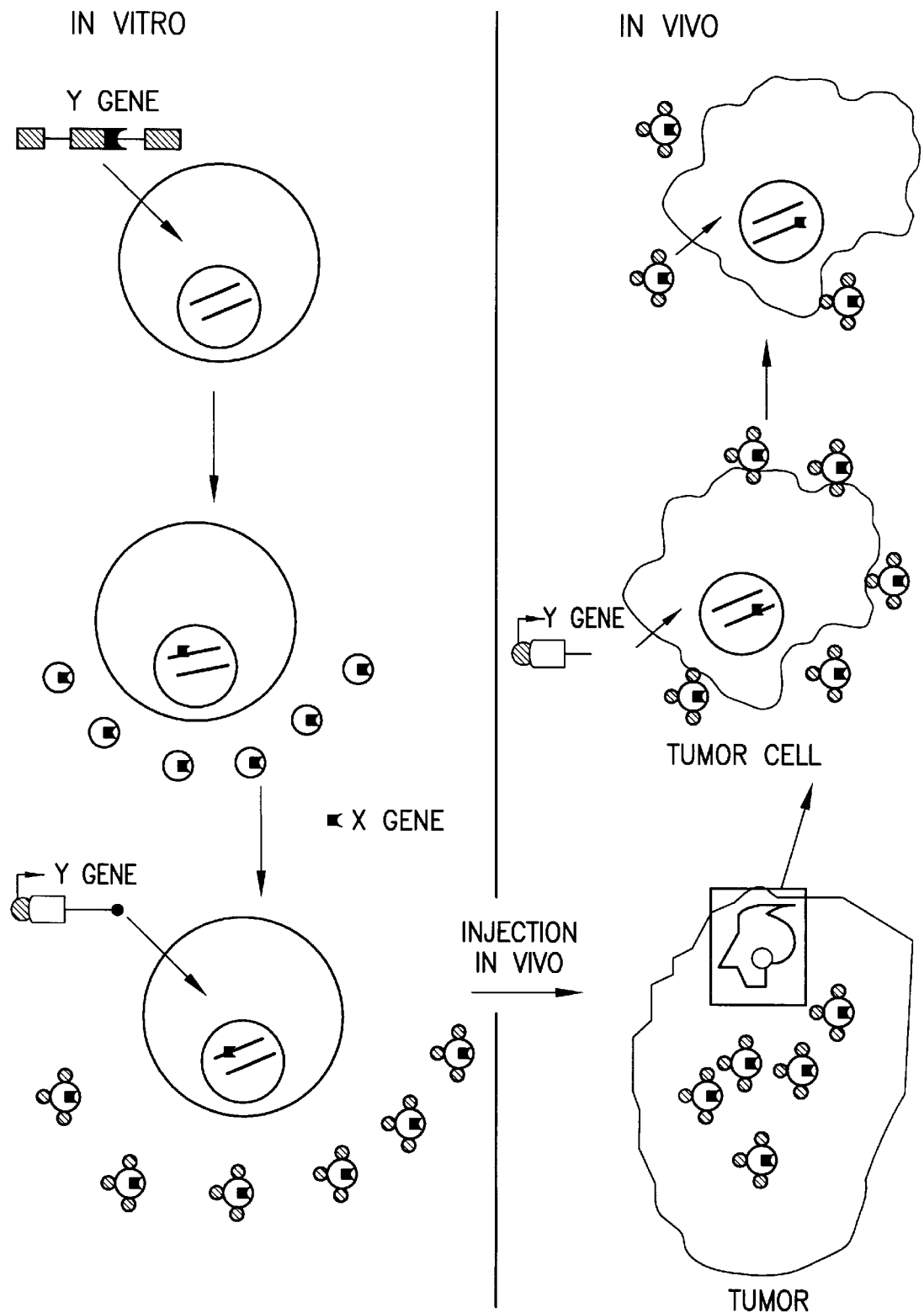

FIG. 3 represents the therapeutic diagram from the generation of the cells producing the infectious viral particles carrying the transgene up to their injection in situ into the tumor as well as the perpetuation of the infectious cycle by in situ complementation with an envelope gene. The left column outlines the production of defective recombinant viral particles as already represented in FIG. 2, which cells are injected in vivo into a tumor. The defective recombinant viral particles produced in situ are then capable of infecting tumor cells; the therapeutic effect of the transgene can then be expressed in these cells and the transduced tumor cells themselves produce viral particles carrying the transgene and lacking an envelope. The cycle stops at this level, unless a vector according to FIG. 1b is subsequently added.

Figure 4A:
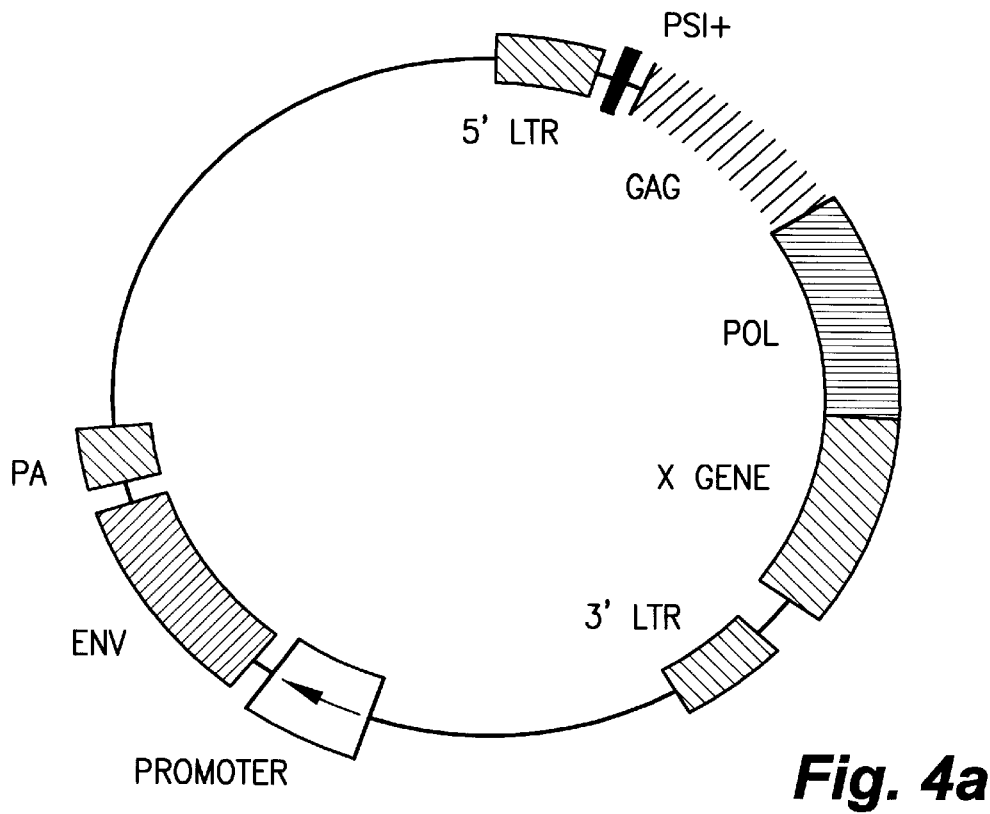

FIG. 4a represents a plasmid construct in which the two—pseudo-retroviral and env.—sequences are carried by the same structure.

Figure 4B:
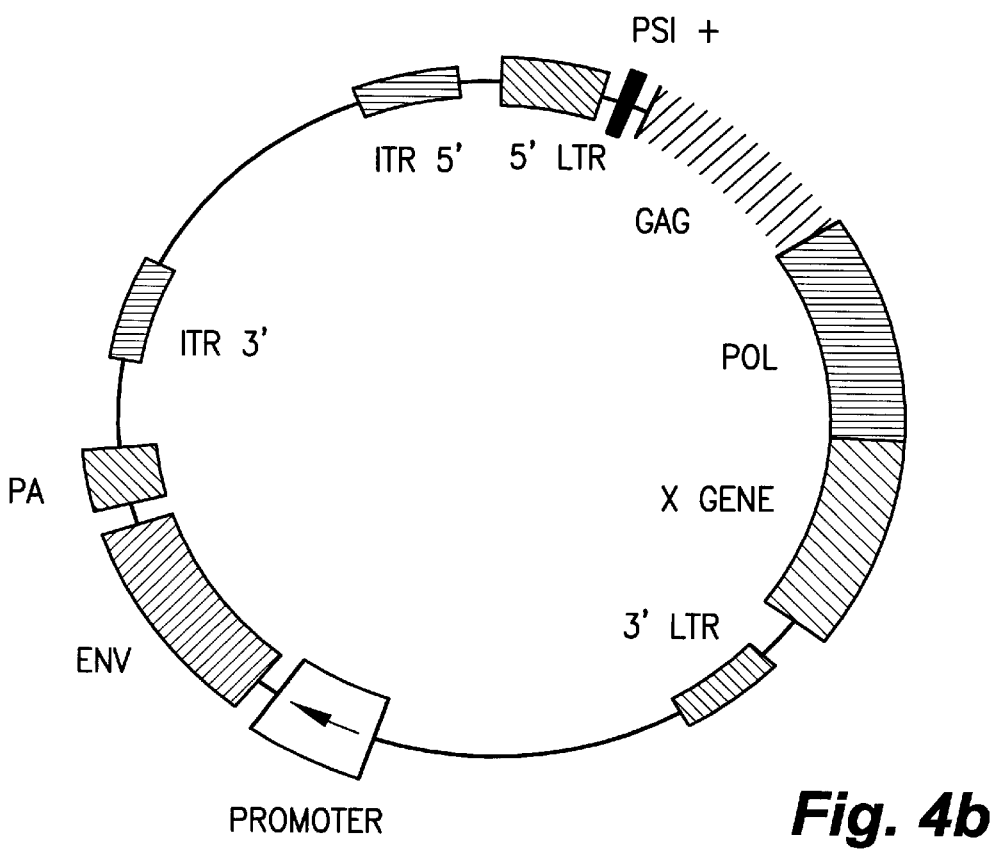

FIG. 4b is a variant in which the ITRs of the AAV virus have been added upstream of the 5' LTR and downstream of the polyademylation (PA) sequence.

The transgene is in both cases the HSV1 thymidine kinase gene.

Figure 5A:
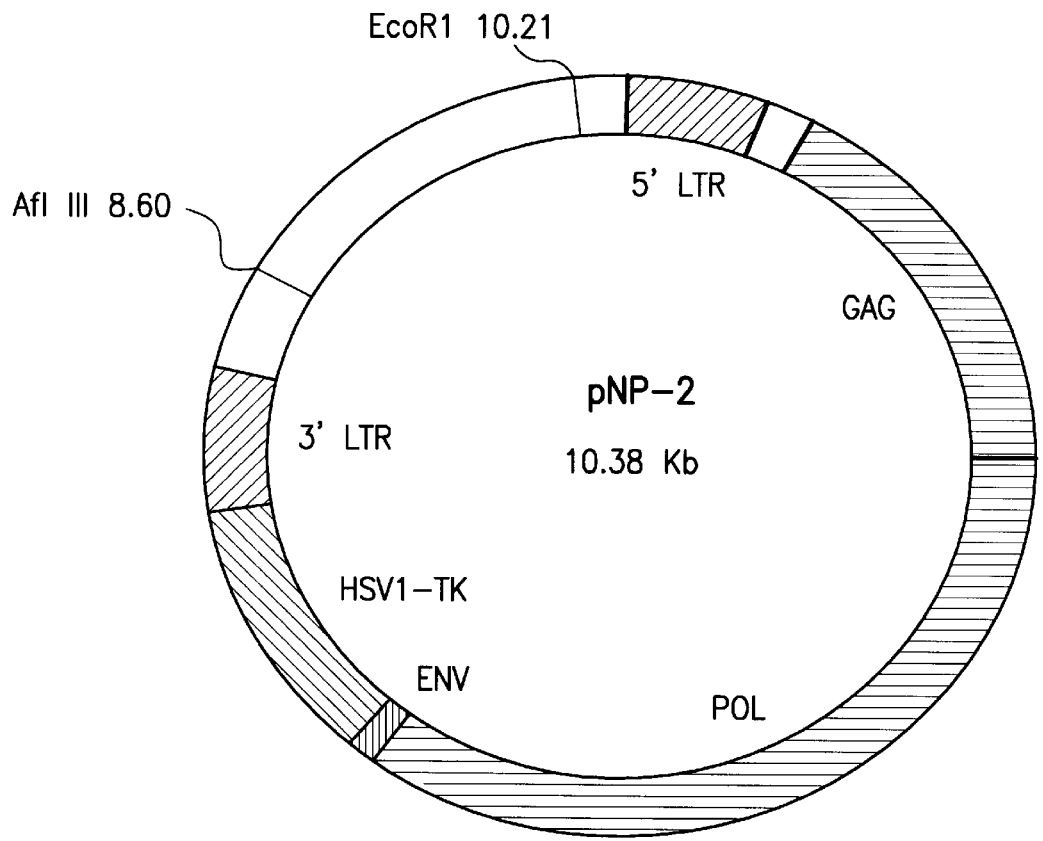
Figure 5B:
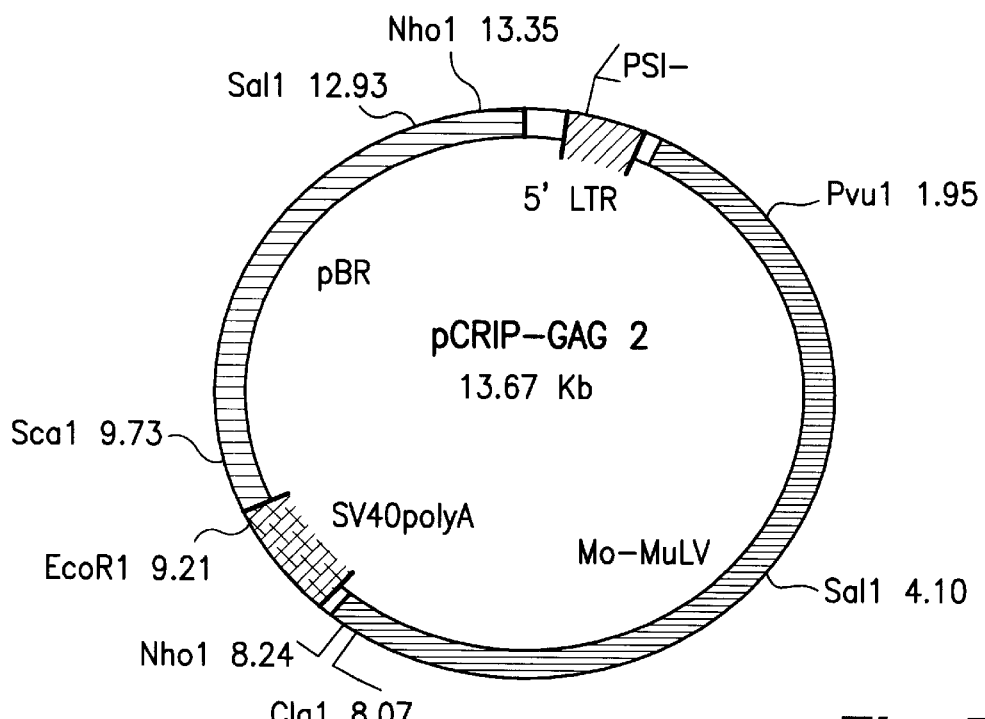

FIG. 5A–5B represent a specific pair of vectors used to show the efficiency of the system of the invention, FIG. 5a being the vector pNP-2 containing the HSV1-TK gene, and FIG. 5b being the plasmid p CRIP GAC-2 containing the Moloney virus env gene, as described in Example 3 below.

EXAMPLE I

Construction of a Moloney virus carrying a therapeutic gene defective for the viral envelope:

The vector used is derived from the retroviral vector pMA 245, which is derived from the Moloney virus MuLV and was constructed from MuLV fragments cloned from different Mov species (Mov-3, -9, and -13) as established by Jaenisch et al., 1981, Cell 24: 519–529.

The genetic construction can be easily performed by persons skilled in the art. A plasmid carrying an infectious Moloney provirus is used as starting material. Such a plasmid, when it is transfected into an appropriate cell line (for example mouse NIH-3T3 cell), gives rise to infectious viral particles carrying the wild-type Moloney genome derived from the transfected genetic construct. In this genome, the gene encoding the envelope is replaced by a gene encoding the protein of therapeutic interest. This construction is performed such that this gene is synthesized from the same spliced transcripts as the "wild-type" envelope gene. For the sake of efficiency of expression of the gene of therapeutic interest, and also of efficiency of production of retroviral particles, the gene of therapeutic interest can even be substituted such that its ATG codon is exactly in the position of the ATG of the Moloney env gene. The gene of therapeutic interest is more easily derived from the complementary DNA and therefore contains no intron and also lacks a polyadenylation sequence. The genetic construction is such that it therefore preserves the natural splicing of the Moloney virus, such that it preserves the reading frame of the gag and pol genes and such that it preserves the integrity of the 3' LTR of the Moloney virus. The entire genetic construction is performed according to the rules of the art by enzymatic digestion of the DNA and then ligation of the appropriate fragments; these techniques are described in Maniatis et al., 1989, Molecular Cloning, A Laboratory Manual. If necessary, it uses PCR or any appropriate amplification technique in order to generate genetic fragments at the ends of which the restriction sites appropriate for the cloning are present.

If necessary also, the different genetic fragments constituting the infectious Moloney provirus can be degraded into shorter fragments distributed over the different plasmids, such that they can be handled more easily in order to be subsequently reassembled in an appropriate manner. If necessary, finally, site-directed mutagenesis can be used to introduce either restriction sites necessary for performing the genetic construction, or in order to substitute the different genes at precise positions. At the end of this genetic construction, a plasmid is available which, when it is transfected into a cell (for example NIH-3T3), is expressed like a wild-type Moloney virus and therefore results in the generation of viral particles whose genome consists of the provirus itself. Because of the homology between the infectious provirus and the newly constructed defective provirus, the synthesis of the different RNAs takes place with an efficiency in optimized proportions which ensure that the number of viral particles which are manufactured by the cell is very similar to that of a wild-type virus. This number of viral particles is therefore considerably greater than that manufactured by conventional encapsidation lines in which the different Moloney virus structural genes are carried by different genetic constructs, and in which the retroviral vector which constitutes the genome of the viral particle is on a different plasmid and has a structure and a size which are very different from those of the wild-type Moloney. It should be noted that the viral particles thus produced are not infectious because they lack an envelope. This envelope protein may be provided independently in this cell by means of a vector whose construction is performed below.

EXAMPLE II

Construction of the nucleic acid sequence carrying the env gene:

It is indeed possible to transfect, into this cell, a new simple genetic construct containing a membrane-expressed gene under the control of a conventional promoter (for example the SV40 virus promoter, a cytomegalovirus promoter, a promoter of a housekeeping gene such as PGK, or even a promoter specific for a given cell type and which will therefore offer an additional safety during use). This expression vector also comprises polyadenylation sequences obtained from different genetic constructs (growth hormone, β-globin and SV40 polyadenylation sequences and the like). The membrane gene may be either an envelope of the Moloney virus itself, or an envelope of another virus which can be captured by the viral particle and expressed at its surface, or even a cell membrane protein which may also be present at the surface of the viral particle. This is the case especially for the CD4 molecule which has been shown to be capable of being incorporated by different retroviruses.

Another embodiment is the construction of chimeric membrane proteins, such that their intracellular part is derived from the intracellular part of the Moloney virus envelope, and their extracellular part is a membrane protein allowing better targeting of the viral particle. The presence of the intracellular regions of the Moloney envelope probably ensures a better efficiency of expression of this chimeric envelope at the surface of the viral particle.

This second genetic construct is also produced such that it contains no sequence derived from a Moloney virus other than the envelope gene itself. More precisely, it cannot contain a sequence which has not previously been deleted on the previous genetic construct. In this way, the possibility of a recombination between this expression vector and the defective retrovirus as was described above is substantially minimized, which recombination could result this time in the production of an infectious Moloney retrovirus. These genetic constructions are also performed according to the rules of the art as indicated above.

EXAMPLE III

Expression of viral particles by transcomplementation of the two sequences constructed in Examples I and II respectively:

The constructs are used to infect myeloma cells p3X63Ag8 or 3T3 TK⁻ cells deficient in thymidine kinase.

The experiment below comprises two control experiments and two tests:

batch a): a first control of selection medium, in which the cells are not transfected, batch b): a second control of the efficiency of the transfection in which the cells are transfected with a plasmid containing a gene encoding β-galactosidase (Lac Z)

batch c): a test in which the cells are transfected with the plasmid pNP-2 alone but which allows the expression of TK but not the propagation via the manufacture of defective recombinant retroviral particles, batch d): a test in which the cells are co-transfected with the vector pNP-2 and a plasmid carrying the env gene of the Moloney virus Mo-MuLV.

III.1 Description of the Plasmids

FIG. 5a represents the plasmid pNP-2 which was deposited at CNCM on Feb. 20, 1995 under No. I-1541. It contains the Mo-MuLV GAG and POL genes, with, down-stream, an HSV1-TK gene under a mutated env gene ATG. Its total size is 10.38 KB. The sites AF III (at 8.60 Kb) and ECoR1 (at 10.21 KB) are represented.

FIG. 5b represents the second plasmid pCRIP GAG-$^{-2}$, which is an example of a construct in which the MoMuLV env gene is integrated into a sequence containing the MoMuLV sequences, ψ−gag−, pol+, env+ and followed downstream by an SV 40 polyA sequence. The figures in bracket indicate the distance in number of base pairs.

III.2 Transfection

3T3 TK cells are either nontransfected (batch a)), or transfected according to the conditions described above (batches b), c) and d)).

In batch b), the transfection efficiency is revealed using a chromogenic substrate; for that, the cells are cultured in the presence of IPTG (induction of Lac operon) and at the end of 24 h in the presence of x gal whose color changes to blue when it is cleaved by the β-galactosidase expressed. The presence of the blue color in the cells therefore reveals the existence of transfection.

In batches c) and d), the cells are placed in the presence of HAT selection medium either at 24 h, or after 5 days of culture when it is expected to have a substantially greater number of cells resistant under HAT, taking the cell propagation into account.

III.3 Results

1) Transfection efficiency: under the conditions used, the efficiency of transfection with the plasmid lac Z shows values at around 5% of transfected cells.

2) Clones obtained after a selection immediately after the 24th hour. For the transfections with the plasmid pNP-2 alone, fewer than about ten clones of very small size are seen (between 20 to 50 cells per clone). For the transfection with pNP-2 plus the gene encoding the Moloney envelope, about ten clones of small size plus 38 clones of considerably larger size (>200 cells per clone) are also seen.

3) Clones obtained after an HAT selection on the 5th day. For the transfections with pNP-2 alone, a few clones, also of small size, are found. For the dish corresponding to the transfection of pNP-2 and the plasmid env, a very large, uncountable, number of clones is observed, corresponding to about a quarter of the confluent state on the dish as a whole.

III.4 Conclusions

1) The plasmid pNP-2 is functional and allows the expression of the TK gene.

2) Immediately after the 24th hour, recombinant viral particles are produced which make it possible to efficiently and stably transfer the TK gene into the cells of the culture.

3) After 5 days, a large increase (but difficult to quantify in this experiment) is observed in the number of stable clones obtained.

EXAMPLE IV

Construction of a single plasmid carrying both the recombinant pseudo-retroviral sequence lacking the env. gene and carrying the HSV1 thymidine kinase, and an env. gene in dependence on a promoter upstream and an env. gene downstream.

A conventional plasmid is used as basic skeleton, for example PBR 322 by the methods described above. The constructs as represented in FIGS. 4a and 4b are produced, the plasmid thus recombined may thus be emulsified and enveloped in liposomes or combined with any other vector which makes it possible to cause it to penetrate into the host cell or into the target cell.

EXAMPLE V

Experimental results obtained on established tumors from the host-vector system obtained with the constructs described in Examples I, II and III:

It was observed that this host-vector system thus constructed produces infectious retroviral particles at a titer of 108 particles/ml.

The titer was checked by infection of mouse L-cells deficient in thymidine kinase and infected according to the method described in Caruso M. et al., Proc. Natl. Acad. Sci. USA, 90:7024–7028, 1993.

In conclusion, the process for treating cells in vivo by gene therapy with the aid of the host-vector system and the medicinal products containing this system as active ingredient appears to be particularly advantageous in the light of the preexisting techniques on the different points mentioned above, namely:

the productivity of the viral particles emitted (at least 1 to 2 logs above the productivity of the conventional packaging cell lines), the operational nature from the point of view of an industrial implementation of the production of a medicinal product using this system since this host-vector system can use host cells capable of being cultured in suspension and therefore on a large scale, an increase in the efficiency of the system from the point of view of the target cells since the production of infectious viral particles carrying the transgene is an iterative process which can be repeated in vivo by addition, with the aid of a vector or of any appropriate means, of a nucleic acid sequence carrying the env gene and in dependence on its promoter; the system may be blocked which makes it possible to stop any dissemination of recombinant viral particles by stopping the addition of the env gene; this makes it possible to control, for example in the case of suicide genes, the number of cells destroyed by addition of nucleoside analogs according to the size of a possible tumor or the number of cells to be destroyed, finally, this system allows great flexibility during use while retaining viral safety and can be applied to any other conditional gene expression system.

We claim:

1. A genetic construct comprising:
   a replication defective viral genome containing a transgene of interest; and
   a nucleic acid coding for product(s) which, in trans, effect the reconstitution of replication defective viral particles containing said replication defective viral genome,
   wherein said nucleic acid is operably linked to a promoter and wherein said nucleic acid and said replication defective viral genome are separately located on the genetic construct.

2. The genetic construct according to claim 1, wherein the replication defective viral genome is a retroviral genome and wherein the nucleic acid comprises a retroviral env gene.

3. The genetic construct according to claim 1, wherein the replication defective viral genome is an adenoviral genome and wherein the nucleic acid comprises an adenoviral E1 region.

4. The genetic construct according to claim 1, further comprising one or two inverted terminal repeat sequences of an adeno-associated virus located outside of the replication defective viral genome and the nucleic acid.

5. A genetic construct comprising:

a replication defective retroviral genome containing a transgene of interest; and a nucleic acid coding for a product which, in trans, effects the reconstitution of replication defective retroviral particles containing said replication defective retroviral genome, wherein said nucleic acid is operably linked to a promoter and wherein said nucleic acid and said replication defective retroviral genome are separately located on the genetic construct.

6. A genetic construct comprising:

a replication defective adenoviral genome containing a transgene of interest; and a nucleic acid coding for a product which, in trans, effects the reconstitution of replication defective adenoviral particles containing said replication defective adenoviral genome, wherein said nucleic acid is operably linked to a promoter and wherein said nucleic acid and said replication defective adenoviral genome are separately located on the genetic construct.

* * * * *